United States Patent [19]
Curran

[11] 3,962,317

[45] June 8, 1976

[54] D-3,6-DIAMINOHEXANOIC ACID 2-(CARBOXYMETHYL)-2-METHYLHYDRAZIDE, PROCESS OF PREPARING AND INTERMEDIATES OF SAID PROCESS

[75] Inventor: William Vincent Curran, Pearl River, N.Y.

[73] Assignee: American Cyanamid Company, Stamford, Conn.

[22] Filed: Aug. 19, 1974

[21] Appl. No.: 498,828

[52] U.S. Cl. .................... 260/482 B; 260/534 R; 424/319

[51] Int. Cl.² ............... C07C 109/97; C07C 125/06

[58] Field of Search ........ 260/471 A, 482 B, 518 R, 260/534 L, 534 R

[56] References Cited
UNITED STATES PATENTS 3,541,135  11/1970  Jöhl et al.......................... 260/482 B Primary Examiner—Richard L. Raymond
Attorney, Agent, or Firm—Edward A. Conroy, Jr.

[57] ABSTRACT

This disclosure describes D-3,6-diaminohexanoic acid 2-(carboxymethyl)-2-methylhydrazide which is useful as an antibacterial agent.

7 Claims, No Drawings

D-3,6-DIAMINOHEXANOIC ACID 2-(CARBOXYMETHYL)-2-METHYLHYDRAZIDE, PROCESS OF PREPARING AND INTERMEDIATES OF SAID PROCESS

BRIEF SUMMARY OF THE INVENTION

This invention relates to a new organic compound, D-3,6-diaminohexanoic acid 2-(carboxymethyl)-2-methylhydrazide, which may be represented by the following structural formula:

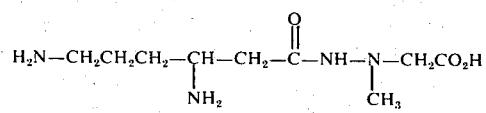

The invention also includes the novel process for preparing this compound as well as the novel intermediates employed in its synthesis. This novel compound is the deoxy analogue of the antibiotic Negamycin which is disclosed in U.S. Pat. No. 3,743,580.

DETAILED DESCRIPTION OF THE INVENTION

The D-3,6-diaminohexanoic acid 2-(carboxymethyl)-2-methylhydrazide of the present invention forms non-toxic acid-addition salts with a variety of pharmacologically acceptable organic and inorganic salt-forming reagents. Thus, acid-addition salts, formed by admixture of the organic free base with an equivalent of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and related acids. For purposes of this invention, D-3,6-diaminohexanoic acid 2-(carboxymethyl)-2-methylhydrazide is equivalent to its non-toxic acid-addition salts. Base derived salts formed by admixture of D-3,6-diaminohexanoic acid 2-(carboxymethyl)-2-methylhydrazide with a base, suitably in a neutral solvent, are formed with such bases as sodium hydroxide, potassium hydroxide, calcium hydroxide, magnesium hydroxide, etc. For purposes of this invention, D-3,6-diaminohexanoic acid 2-(carboxymethyl)-2-methylhydrazide is equivalent to its non-toxic alkali metal and alkaline earth metal salts.

The novel compound of the present invention is useful as an antimicrobial agent and possesses broad-spectrum antibacterial and antifungal activity in vitro against a variety of standard laboratory microorganisms as determined by the standard agar well diffusion assay. In this assay, the minimal inhibitory concentration (MIC) was determined by using twofold dilutions of the compound in nutrient agar. One ml. of each dilution was placed in a sterile Petri dish; 9 ml. of nutrient agar was added to each dish. Five hour cultures of the indicated organism in Trypticase Soy Broth were diluted $10^{-2}$ in nutrient broth. This dilution of each culture was transferred to the surface of the plates by using a Steers replicating device. After incubation at 37°C. for 24 hours, the MIC was recorded as the lowest concentration of the compound which completely inhibits the macroscopic growth of each organism. The MIC of D-3,6-diaminohexanoic acid 2-(carboxymethyl)-2-methylhydrazide against the indicated organisms are set forth in Table I below.

TABLE I

| Culture | Strain Designation | MIC (mcg./ml.) |
|---|---|---|
| Escherichia coli | K-1972-1 | 16 |
| Escherichia coli | K-1972-2 | 16 |
| Enterobacter sp. | K-1972-1 | 32 |
| Klebsiella pneumoniae | K-1972-2 | 32 |
| Proteus mirabilis | K-1972-12 | 64 |
| Proteus mirabilis | K-1972-16 | 64 |
| Proteus vulgaris | K-1972 | 64 |
| Pseudomonas aeruginosa | PA$_7$ | 64 |
| Pseudomonas aeruginosa | 12-4-4 | 64 |
| Salmonella typhimurium | K-1972 | 32 |
| Salmonella enteritidis | K-1972 | 32 |
| Shigella flexneri (2a) | RB | 4 |
| Shigella flexneri (5) | Citarella | 64 |
| Serratia marcescens | Finland | 64 |
| Serratia marcescens | K132 | 32 |
| Herellea vaginicola | Washington 885-863 | 32 |
| Herellea vaginicola | Hughes | 32 |
| Staphylococcus aureus | Morton No. 1169 | 32 |
| Staphylococcus aureus | Jackson No. 4 | 64 |
| Enterococcus (S. faecalis) | Isenberg | >128 |
| Escherichia coli | No. 311 | 16 |
| Proteus mirabilis | No. 4361 | 64 |
| Klebsiella pneumoniae | AD | 4 |

In another representative operation, the standard agar well diffusion assay was repeated with D-3,6-diaminohexanoic acid 2-(carboxymethyl)-2-methylhydrazide except that after incubation the zone of inhibition against the indicated organism is millimeters was determined. The results are set forth in Table II below.

TABLE 2

| Name of Organism | Zone of Inhibition mm. |
|---|---|
| Mycobacterium smegmatis ATCC 606 | 100 |
| Staphylococcus aureus Rose ATCC 14154 | 100 |
| Enterobacter aerogenes 75 | 50 |
| Escherichia coli 311 | 25 |
| Klebsiella pneumoniae AD | 10 |
| Proteus vulgaris ATCC 9484 | 25 |
| Pseudomonas aeruginosa ATCC 10145 | 50 |
| Salmonella typhosa ATCC 6539 | 25 |
| Candida albicans E 83 | 50 |
| Cryptococcus neoformans E 183 | 10 |
| Microsporum canis ATCC 10214 | 250 |
| Trichophyton tonsurans NIH 662 | 25 |
| Trichophyton mentagrophytes E11 | 100 |

The novel compound of the present invention is also active in vivo against Proteus mirabilis and Escherichia coli and controlled systemic lethal infections of these two organisms in mice. The infections were administered to the mice as follows:

Proteus mirabilis 4671: intraperitoneal injection of a lethal dose consisting of 0.5 ml. of a $10^{-1.6}$ trypticase soy dilution of a 5 hour trypticase soy broth culture.

Escherichia coli 311: intraperitoneal infection of a lethal dose consisting of 0.5 ml. of a $10^{-3}$ trypticase soy dilution of a 5 hour trypticase soy broth culture.

The D-3,6-diaminohexanoic acid 2-(carboxymethyl)-2-methylhydrazide was administered as follows:

Proteus mirabilis 4671: 0.5 ml. dose suspended in 0.2% aqueous agar was administered to groups of Charles River CD1 female mice, weighing 18–22 gm., 1 day prior to infection and then in a second dose immediately after infection at the levels indicated in Table III below.

*Escherichia coli* 311: 0.5 ml. dose suspended in 0.2% aqueous agar was administered to groups of Charles River CD1 female mice, weighing 18–22 gm., immediately after infection at the levels indicated in Table III below.

TABLE III

| Infection | Dose Subcutaneous (mg./kg.) | Alive/Total Mice Tested 7 Days After Infection |
| --- | --- | --- |
| *Proteus mirabilis* 4671 | 256 | 5/5 |
|  | 128 | 5/5 |
|  | 64 | 5/5 |
| *Escherichia coli* 311 | 64 | 5/5 |
|  | 32 | 3/5 |
|  | 16 | 0/5 |
|  | 8 | 0/5 |
|  | 4 | 0/5 |
| Infected non-treated Controls | — | 3/20 |

As an antimicrobial the compound of this invention may be administered orally or parenterally in the usual pharmaceutical forms, or possibly in the diet, and/or as compositions of the active ingredient in an edible carrier. Such compositions may include tablets, scored or unscored, or hard or soft shell capsules. Excipients may include lactose, starch, buffers, disentegrating agents, lubricants, homogenizing agents, and the like. Oral and parenteral compositions may include similar agents and also preservatives, emulsifiers, surfactants, stabilizers and the like in solutions, suspensions, syrups, elixirs, etc. in either aqueous or non-aqueous systems. Additional excipients might include sweeteners, flavorings, colorings, or perfumes. Topical preparations, it is expected, will prove particularly useful. Such compositions would be designed for administration to subjects exposed to, or infected with sensitive bacteria or fungi for either treatment or prophylaxis and may include, in addition to the foregoing, ointments, creams, emulsions, unguents, salves, emollients, and the like. In addition, the compound of this invention may be used in the form of solutions, suspensions, washes, powders, dusts, mists, soaps, sprays, aerosols, drenches, or other forms for the purpose of cleaning, disinfecting, or sterilizing surgical instruments, laboratory glassware or instruments, hospital walls or other surfaces, linens, dishes, laboratory tables, coops, cages, or the like. Likewise the compound might be incorporated into soaps, detergents, sprays or the like in the home, farm, office or elsewhere with the purpose of preventing or minimizing infection or contamination with sensitive bacteria or fungi. Painting, spraying, immersion or other means of effecting contact may be applied.

The invention will be described in greater detail in conjunction with the following specific example.

EXAMPLE 1

Preparation of N,N'-dicarbobenzoxy-D-ornithine

A solution of D-ornithine monohydrochloride in 60 ml. of 2N sodium hydroxide was cooled to 5°C. Carbobenzoxy chloride (20.4 g.) and 2N sodium hydroxide (64 ml.) were added in four equal portions over 1.0 hour with stirring. The mixture was stirred for an additional 0.5 hour in the cold, then extracted with diethyl ether. The aqueous portion was chilled and acidified (25 ml. 6N hydrochloric acid) and the resulting oil was extracted into ether containing some ethyl acetate. The organic phase was extracted with water, then saturated salt solution and dried ($MgSO_4$). Evaporation of the solvent gave an oil which crystallized from ether to afford 18.8 gms. of product, m.p. 110.5°–113°C.

EXAMPLE 2

Preparation of N,N'-dicarbobenzoxy-D-β-lysine, methyl ester

N,N'-Dicarbobenzoxy-D-ornithine (5.0 g.) and phosphorus pentachloride (2.75 g.) in 100 ml. of diethyl ether was stirred in an ice bath for 3.0 hours. Hexane (80 ml.) was added and the white crystalline product was collected by filtering. This product was slurried in ether (100 ml.) and added to 200 ml. of a cold, ethereal solution of diazomethane (prepared from 10 g. of N-methyl-N'-nitro-N-nitrosoguanidine.) The mixture was allowed to stand in the cold for 1.0 hour, then at room temperature overnight. The excess diazomethane was destroyed with acetic acid and the reaction mixture was evaporated at reduced pressure. The resulting light yellow crystals were dissolved in methanol (50 ml.) and a freshly prepared solution of silver benzoate (0.5 g.) in triethylamine (10 ml.) was added. The mixture was stirred at room temperature for 1.0 hour, heated to boiling, filtered, and evaporated under reduced pressure. The resulting oil was crystallized and recrystallized from ethyl acetate:hexane to give 2.2 g. of white crystals, m.p. 100°–102°C.

EXAMPLE 3

Preparation of N,N'-dicarbobenzoxy-D-β-lysine

N,N'-dicarbobenzoxy-D-β-lysine, methyl ester (2.0 g.) was added to a solution of 20 ml. of 1N sodium hydroxide in methanol: tetrahydrofuran (50 ml.:15 ml.) and the mixture was stirred at room temperature for 1.5 hours. The reaction mixture was acidified with concentrated hydrochloric acid (2 ml.), diluted with water (25 ml.), and filtered to afford 1.7 g. of crystals, m.p. 152°–154°C.

EXAMPLE 4

Preparation of D-3,6-di(benzyloxycarbonylamino)-hexanoic acid 2-(carbethoxymethyl)-2-methylhydrazide To a cold solution of N,N'-dicarbobenzoxy-D-β-lysine (1.5 g.) and N-methylmorpholine (0.4 mg.) dissolved in 25 ml. of tetrahydrofuran was added isobutyl chloroformate (0.48 ml.). The mixture was stirred in the cold for 15 minutes, then a cold mixture of ethyl 1-methyl-hydrazinoacetate hydrochloride (0.61 g.) and N-methyl-morpholine (0.4 ml.) in 25 ml. of tetrahydrofuran was added. The reaction mixture was stirred in the cold for 15 minutes, at room temperature for 3 hours, then brought to boiling, cooled and poured into water. The aqueous solution was extracted with ethyl acetate and the organic extract was washed with water, dilute hydrochloric acid, saturated sodium bicarbonate, and then dried over magnesium sulfate. Evaporation of the solvent left an oil which was crystallized from ethyl acetate:hexane to afford 1.5 g., m.p. 118.5°–120°C.

EXAMPLE 5

Preparation of
D-3,6-di-(benzyloxycarbonylamino)-hexanoic acid
2-(carboxymethyl)-2-methylhydrazide A solution of D-3,6-di-(benzyloxycarbonylamino)-hexanoic acid 2-(carbethoxymethyl)-2-methylhydrazide (1.0 g.) in 10 ml. of methanol containing 3 ml. of 1N sodium hydroxide was stirred at room temperature for 20 minutes, then poured into 50 ml. of water. The solution was acidified with concentrated hydrochloric acid (0.3 ml.) and extracted with ethyl acetate. The ethyl acetate solution was extracted with water, dried (magnesium sulfate) and evaporated to give 0.65 g. of a white crystalline product, m.p. 113.5°–115°C.

EXAMPLE 6

Preparation of D-3,6-diaminohexanoic acid
2-(carboxymethyl)-2-methylhydrazide

A solution of D-3,6-di(benzyloxycarbonylamino)-hexanoic acid 2-(carboxylmethyl)-2-methylhydrazide (0.5 g.) in 50 ml. of methanol was hydrogenated at atmospheric pressure over 10% palladium on carbon until the evolution of carbon dioxide ceased. Evaporation of solvent gave the product as a glass-like solid.

I claim:

1. A compound selected from the group consisting of D-3,6-diaminohexanoic acid 2-(carboxymethyl)-2-methylhydrazide, the pharmacologically acceptable acid-addition salts thereof, the pharmacologically acceptable alkali metal salts thereof, and the pharmacologically acceptable alkaline earth metal salts thereof.

2. D-3,6-Di(benzyloxycarbonylamino)-hexanoic acid 2-(carboxymethyl)-2-methylhydrazide.

3. D-3,6-Di(benzyloxycarbonylamino)-hexanoic acid 2-(carbethoxymethyl)-2-methylhydrazide.

4. N,N'-Dicarbobenzoxy-D-β-lysine.

5. N,N'-Dicarbobenzoxy-D-β-lysine, methyl ester.

6. N,N'-dicarbobenzoxy-D-ornithine.

7. The process of preparing D-3,6-diaminohexanoic acid 2-(carboxymethyl)-2-methylhydrazide which comprises the steps of a. converting N,N'-dicarbobenzoxy-D-ornithine to the corresponding acid chloride (I) by treatment with phosphorus pentachloride in diethyl ether,

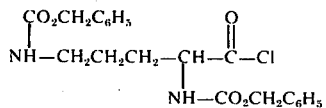   (I)

b. treating said acid chloride with diazomethane in diethyl ether to form the diazoketone (II),

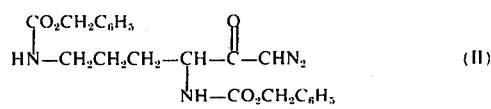   (II)

c. converting said diazoketone to the D-β-lysine derivative (III) by treatment with silver benzoate and triethylamine in methanol,

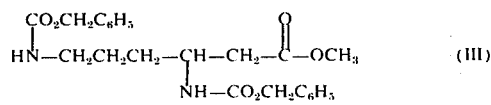   (III)

d. hydrolyzing said D-β-lysine derivative under basic conditions to form the free acid (IV),

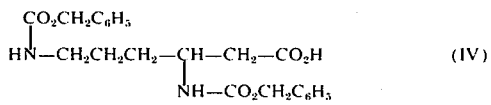   (IV)

e. coupling said free acid with ethyl N-methylhydrazinoacetate in tetrahydrofuran in the presence of N-methylmorpholine and isobutyl chloroformate to form D-3,6-di(benzyloxycarbonylamino)-hexanoic acid 2-(carbethoxymethyl)-2-methylhydrazide (V),

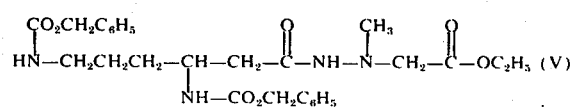   (V)

f. hydrolyzing said hydrazide ester under basic conditions to form the free acid (VI), and

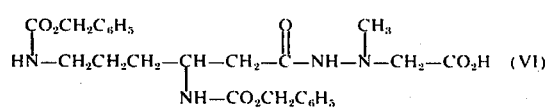   (VI)

g. hydrogenating said free acid in methanol in the presence of 10% palladium on carbon.

* * * * *